United States Patent [19]

LaRosa

[11] 4,084,910
[45] Apr. 18, 1978

[54] DISPOSABLE SELF-CONTAINED LIQUID APPLICATOR

[75] Inventor: John LaRosa, New Milford, N.Y.

[73] Assignee: International Paper Company, New York, N.Y.

[21] Appl. No.: 704,776

[22] Filed: Jul. 13, 1976

[51] Int. Cl.² .............................................. B43K 5/14
[52] U.S. Cl. ...................................... 401/133; 222/92; 206/603
[58] Field of Search ................................ 401/132–135; 178/269; 222/541, 92; 206/498

[56] References Cited

U.S. PATENT DOCUMENTS

| 2,031,990 | 2/1936 | Turner | 401/132 |
| 3,986,640 | 10/1976 | Redmond | 222/92 |
| 3,998,559 | 12/1976 | Hoyt | 401/132 |

Primary Examiner—Stephen C. Pellegrino
Attorney, Agent, or Firm—Finnegan, Henderson, Farabow & Garrett

[57] ABSTRACT

A disposable self-contained liquid applicator having a rupturable membrane for sealing a container for liquids, an absorbent applicator overlying the membrane for receiving the liquid from the container when the membrane is ruptured, and a member underlying the membrane for producing a rupturing surface and for penetrating the membrane upon actuation by a force applied to the outside of the applicator. The member underlying the membrane includes two integral planar sections inclined from each other and intersecting to define a bending line and at least one serrated slit formed in at least one of the sections along the bending line under the rupturable membrane. The serrated slit has teeth-like edges in the plane of at least one of the sections for forming the rupturing surface and for penetrating the membrane when the edges are moved outwardly against the membrane. The planar sections having outer flange portions extending away from the container which are manually movable downwardly and inwardly toward the container for producing the teeth-like edges from the plane of the sections and for moving the edges outwardly against the membrane.

15 Claims, 5 Drawing Figures

U.S. Patent      April 18, 1978      4,084,910
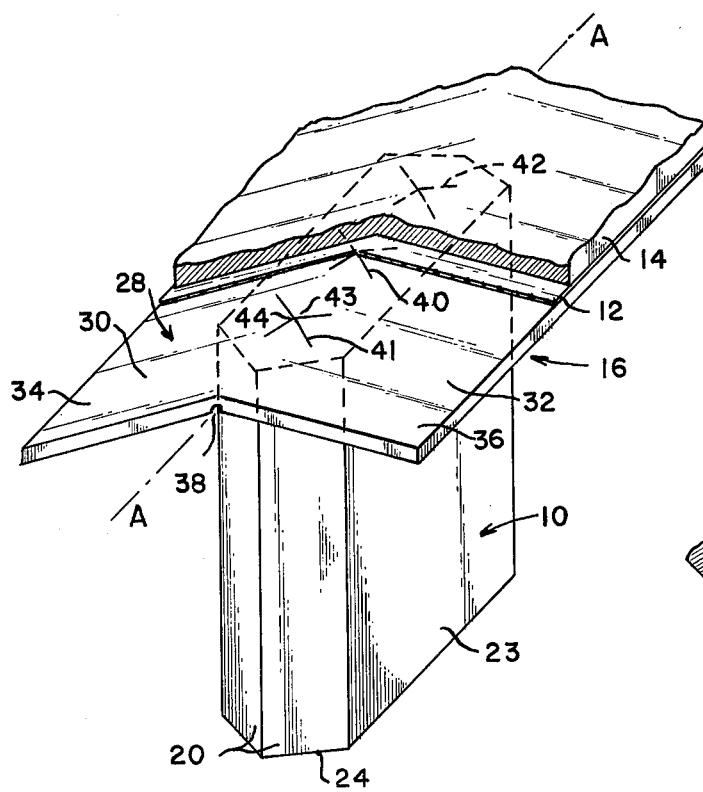
Fig. 1
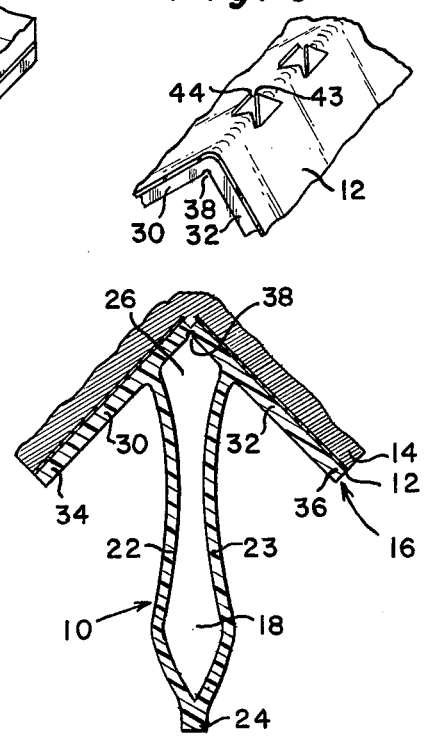
Fig. 5
Fig. 3
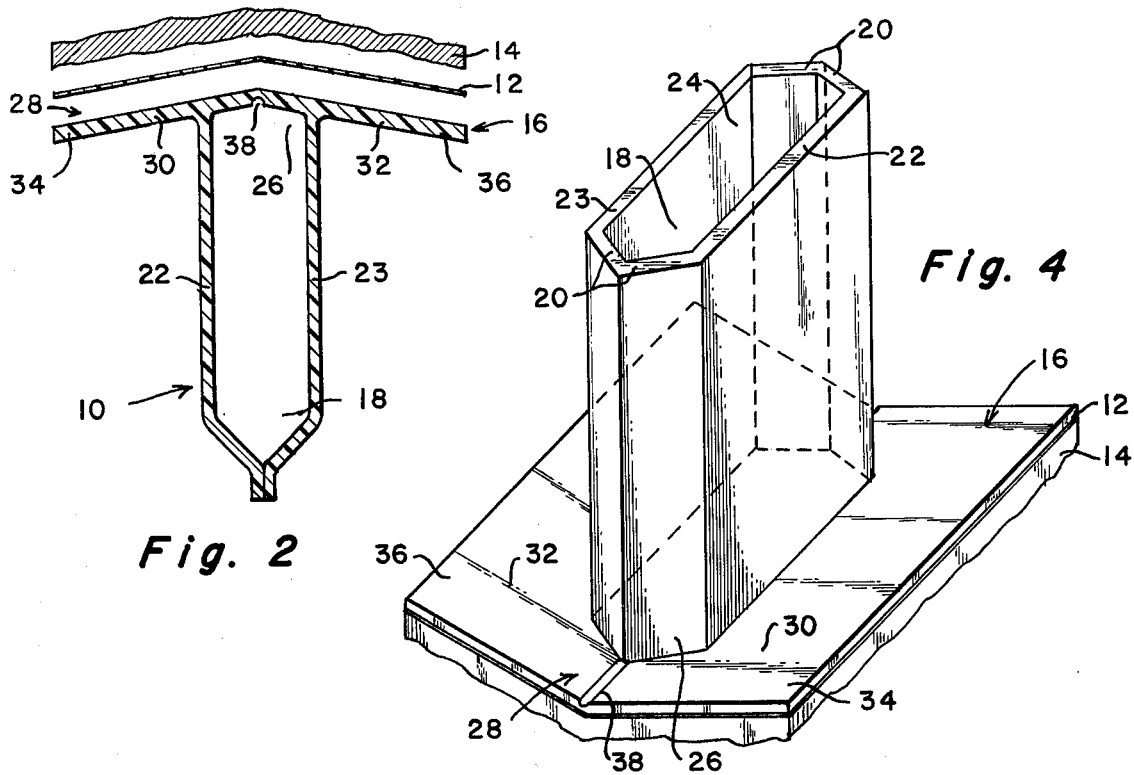
Fig. 2
Fig. 4

DISPOSABLE SELF-CONTAINED LIQUID APPLICATOR

BACKGROUND OF THE INVENTION

The present invention relates to a liquid applicator and, more particularly, to a disposable self-contained liquid applicator.

The liquid applicator of the invention is particularly well suited as an applicator for use in the medical field for applying an antiseptic solution. A prime consideration is to provide a disposable applicator which is easily and inexpensively manufactured and which has a metered amount of antiseptic solution self-contained in a sterile condition. It is important to ensure that the antiseptic solution does not become contaminated prior to usage, and that the container of the applicator be truly sealably closed.

It is also desirable to reduce the possibility of contamination of the application or cleansed surface by the operator when the applicator is being used. Additionally, it is desirable to prevent the soiling of the operator's hand with the solution which is to be applied when the applicator is activated.

In the prior art, while disposable self-contained liquid applicators have been developed, there have been few that have been developed that satisfactorily meet all the previously mentioned requirements, such as in the medical field, and which are additionally reliable and quickly and easily operated. In the prior art, applicators utilize an extraneous rupturing member for opening the liquid container, can be operated only with two hands, provide a less reliable rupturing of a sealing member or less accurate fluid flow path to the absorbent applicator material, or provide an inadequate absorbent applicator surface area or support of the absorbent applicator surface area.

SUMMARY OF THE INVENTION

The disposable self-contained liquid applicator of the invention comprises a container for liquids, a rupturable membbrane for sealing the container, absorbent applicator means overlying the membrane for receiving liquid from the container when the membrane is ruptured, and means underlying the membrane for producing a rupturing surface and for penetrating the membrane upon actuation by a force applied to the outside of the applicator.

Preferably, the means for producing a rupturing surface and for penetrating the membrane includes a member having two planar sections inclined from each other and intersecting to define a bending line and a plurality of serrated slits formed in the sections along the bending line under the membrane. The slits have teeth-like edges in the plane of at least one of the sections for forming the rupturing surface and penetrating the membrane when the edges are moved outwardly against the membrane. The planar sections have outer flange portions extending away from the container which are movable downwardly and inwardly toward the container for producing the teeth-like edges from the plane of the sections and for moving the edges outwardly against the membrane.

It is also preferred that the container and means for producing the rupturing surface and for penetrating the membrane be formed of a single piece of molded material.

This invention thus provides a new and improved liquid applicator that is disposable and which holds a self-contained metered amount of liquid. Numerous other advantages may be attained by practice of the invention. For example, a new and improved disposable self-contained liquid applicator is provided which is reliable and dependable, and which can be easily operated, in particular, with one hand activation.

This new and improved disposable self-contained liquid applicator can also provide a larger absorbent applicator surface area and better support of that absorbent applicator surface area.

Finally, this new and improved disposable self-contained liquid applicator provides the advantages of having a noncontaminated tightly-sealed storage of a liquid solution, preventing the soiling of the operator's hand with the liquid solution when activated, and reducing the possibility of the operator's hand from contaminating the liquid application area during use of the applicator.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims.

BRIEF DESCRIPTION OF THE DRAWING

The accompanying drawing, which is incorporated in and constitutes a part of this specification, illustrates one embodiment of the invention and, together with the description serves to explain the principles of the invention.

FIG. 1 is a perspective view of the disposable self-contained liquid applicator constructed in accordance with the teachings of this invention with the rupturable membrane and absorbent applicator means partially cut away;

FIG. 2 is a sectional view of the disposable self-contained liquid applicator of FIG. 1 with the various parts of the applicator separated from one another;

FIG. 3 is a sectional view of the disposable self-contained liquid applicator of FIG. 1 when a force is applied and the applicator is being activated;

FIG. 4 is a perspective view of the disposable self-contained liquid applicator with one end of the liquid container open in an as-molded, liquid-filling position; and FIG. 5 is a perspective view of the slits and teeth-like edges of the disposable self-contained liquid applicator of FIG. 3 when the force is applied and the applicator is being activated.

DESCRIPTION OF THE PREFERRED EMBODIMENT

Reference will now be made in detail to the present preferred embodiment of the invention, an example of which is illustrated in the accompanying drawing.

As best seen in FIGS. 1 and 2, the disposable self-contained liquid applicator in accordance with the invention comprises a container 10, a rupturable membrane 12, an absorbent applicator means 14, and means 16 for producing a rupturing surface and for penetrating the membrane 12.

In accordance with the invention, the container 10 of the applicator is provided to hold an amount of liquid, such as antiseptic solution, within a chamber 18, defined by the walls of the container 10. The quantity of liquid to be applied to the absorbent applicator means 14 will vary according to the amount of liquid held in the chamber 18. The amount of liquid contained in chamber 18 is dependent upon the metered filling of the liquid and variations in the size and shape of the chamber 18 and container 10.

Preferably, and as best seen in FIG. 4, the container 10 has a cylindrical configuration with a hexagonal cross section with two opposing sides 22 and 23 of the container 10 being greater in width than the remaining four sides 20. Referring again to FIG. 4, it is also preferred that the container 10 be formed of a molded, elastomeric, deformable material with one end 24 molded in an open position and the other end 26, while molded in an open position, closed by the rupturable membrane 12.

In accordance with the invention, the rupturable membrane 12 seals the container 10. As shown in this embodiment, the rupturable membrane 12 is utilized to close end 26 of the container 10 to create a liquid and vapor-tight seal to the end 26 of the chamber 18 in which the liquid will be stored. The rupturable membrane may be made of a material such as a lamination of aluminum foil, polyester film, and polyethylene film.

In the manufacture of the disposable self-contained liquid applicator, once the end 26 of the container 10 is closed and sealed by the rupturable membrane 12, the chamber 18 is filled with the liquid through the open end 24 of the container 10. After filling the chamber 18 with liquid, the open end 24 of the chamber 18 is sealed shut by conventional means, such as heat sealing. The closed configuration of the end 24 is best seen in FIG. 2.

In accordance with the invention, the absorbent applicator means 14 overlies the rupturable membrane 12 for receiving the liquid from the chamber 18 of the container 10 when the membrane 12 is ruptured. The absorbent applicator means 14 may be made of a polyurethane foam, cotton, or any other suitable absorbent material. Preferably, the absorbent applicator means 14 is affixed permanently to the surface of the rupturable membrane 12. During the manufacture of the disposable self-contained liquid applicator, it is preferred that the absorbent applicator means 14 be affixed before the container 10 is filled with liquid and the end 24 of the container 10 is sealed.

In accordance with the invention, the means 16 underlies the rupturable membrane 12, and produces a rupturing surface and penetrates the membrane 12 upon actuation by a force applied to the exterior of the applicator. Referring to FIGS. 1 and 2, the means 16 preferably comprises a member 28 having two planar sections 30 and 32 inclined from each other and intersecting to define a bending line shown in FIG. 1 as line A—A. The bending line A—A defined by sections 30 and 32 run over the end 26 of the container 10 between and parallel to the wider sides 22 and 23 of the container 10.

In the preferred embodiment, the member 28 is generally rectangular shaped with the planar sections 30 and 32 positioned transversely over the end 26 of the container 10. The planar sections 30 and 32 preferably form an underlying supporting surface upon which the rupturable membrane 12 can be positioned and affixed for sealing the end 26 of the container 10.

In this preferred embodiment, the planar sections 30 and 32 underlying the rupturable membrane 12 also provide support to the absorbent applicator means 14 which overlies and is affixed to the surface of the rupturable membrane 12. Therefore, when liquid is received by the absorbent applicator means 14, the planar sections 30 and 32 provide support to a fairly large surface area of the absorbent applicator means 14. This is advantageous because it allows application of the liquid by the absorbent applicator means over a broader application area.

As best seen in FIGS. 1 and 2, it is preferred that the planar sections 30 and 32 have, respectively, outer flange portions 34 and 36 extending respectively away from the wider sides 22 and 23 of the container 10. The flange portions 34 and 36 are provided for manual movement downwardly and inwardly respectively toward the sides 22 and 23 of the container 10, as best seen in FIG. 3.

It is preferred that the two inclined planar sections 30 and 32 be integrally formed of a single piece of molded plastic material. However, the material must be of sufficient rigidity and thickness to allow only a bending of the two planar sections 30 and 32 along bending line A—A. As best seen in FIG. 2, it is preferred that the planar sections 30 and 32 and the container 10 be formed of a single piece of molded material. The planar sections 30 and 32 and the container 10 thus form a cross section which is substantially T-shaped. When the container 10 and the planar sections 30 and 32 are formed of a single piece of molded plastic elastomeric material, the planar sections 30 and 32 are molded with a slightly greater thickness than the sides 22 and 23 of the container 10 in order to provide rigidity when the outer flange portions 34 and 36 of sections 30 and 32 are moved manually downwardly and inwardly toward the container sides 22 and 23 and to ensure a bending of the sections 30 and 32 only along bending line A—A.

To further ensure the downward and inward movement of the flange portions 34 and 36 and bending along bending line A—A, it is preferred that a groove 38 be formed in the under surface of the planar sections 30 and 32 along the bending line A—A. Groove 38 can be formed in the planar sections 30 and 32 in a manner that preserves the integrity of the vapor and liquid-tight seal of the chamber 18.

It is preferred that the member 28 further comprise at least one serrated slit 40 formed in at least one of the planar sections 30 and 32 along the bending line A—A. In the preferred embodiment, as seen in FIG. 1, there are shown three serrated slits 40, 41, and 42 which are positioned in both of the planar sections 30 and 32 along the bending line A—A over the end 26 of the container 10 and which are in communication with the chamber 18 holding the liquid. The slits 40, 41, and 42 are also underlying the rupturable membrane 12 along the bending line A—A.

Preferably, each of the slits 40, 41, and 42 has teeth-like edges 43 and 44 in the plane of at least one of the two planar sections 30 and 32 along the bending line A—A for forming the rupturing surface and for penetrating the membrane 12 when the edges 43 and 44 are moved outwardly against the membrane 12. In the preferred embodiment, the groove 38 previously mentioned as being formed in the under surface of the planar sections 30 and 32 not only ensures downward and inward movement of the flange portions 34 and 36, but also ensures outward movement of the teeth-like edges 43 and 44 against the membrane 12 as the flange portions 34 and 36 produce the edges 43 and 44 from the planar sections 30 and 32. In the maufacture of the disposable self-contained liquid applicator, it is preferred that the planar sections 30 and 32 of member 28 be molded with the slits 40, 41, and 42 so as to avoid additional machining time and cost.

Referring now to FIG. 3, to operate the preferred embodiment of the disposable self-contained liquid applicator, the operator may grasp the outer flange portions 34 and 36 of the two inclined planar sections 30 and 32 between the thumb and forefingers of one hand. When pressure is applied with the thumb and forefingers, the outer flange portions 34 and 36 are moved respectively downwardly and inwardly toward the sides 22 and 23 of the container 10.

By this manual action and due to the combined effect of the rigidity of the planar sections, the configuration of the container 10, the flexibility of sides 22 and 23, and the groove 38, the two planar sections 30 and 32 bend along bending line A—A. The bending movement of the two planar sections 30 and 32 along bending line A—A causes the teeth-like edges 43 and 44 to be produced from the plane of each of the slits 40, 41, and 42 in the sections 30 and 32 and moved outwardly against the rupturable membrane 12. When the teeth-like edges 43 and 44 are moved outwardly against the membrane, the membrane 12 is ruptured and fluid communication is provided from the chamber 18 holding the liquid, through the slits 40, 41, and 42 and the ruptured membrane 12, to the absorbent applicator means 14.

Due to the design of the preferred embodiment of this invention, the operator can grasp the wider sides 22 and 23 of the container 10 and apply the liquid from the absorbent applicator means 16 onto the application surface so that the operator's hand can be kept away from the point of application and thus reduce the possibility of contamination of the cleansed area by the operator. Additional liquid can be expelled from the chamber 18 by applying manual pressure against the sides 22 and 23.

It will be apparent to those skilled in the art that various modifications and variations could be made in the disposable self-contained liquid applicator of the invention without departing from the scope or spirit of the invention.

What is claimed is:

1. A disposable self-contained liquid applicator comprising:
   a container for liquids;
   a rupturable membrane for sealing said container;
   absorbent applicator means overlying said membrane for receiving liquid from said container when said membrane is ruptured; and
   means underlying said membrane for producing a rupturing surface and for penetrating said membrane upon actuation by a force applied to the outside of the applicator said latter means being formed of a single piece of material and including a member having two planar sections intersecting to define a bending line and at least one serrated slit formed in said member along said bending line under said membrane, and wherein said slit has teeth-like edges in the plane of at least one of said planar sections for forming the rupturing surface and penetrating said membrane, said edges being moved outwardly against said membrane upon actuation of said means for producing a rupturing surface and for penetrating said membrane, wherein said planar sections have outer flange portions extending away from said container, said flange portions being manually moved downwardly and inwardly toward said container for producing said teeth-like edges from the sections of said member and for moving said edges outwardly against said membrane.

2. The disposable self-contained liquid applicator of claim 1 wherein said two planar sections are inclined from each other along said bending line.

3. The disposable self-contained liquid applicator of claim 1 wherein a groove is formed in the under surface of said planar sections along said bending line for ensuring downward and inward movement of said flange portions and outward movement of said produced teeth-like edges against said membrane.

4. The disposable self-contained liquid applicator of claim 1 wherein said flange portions may be manually movable by the thumb and fingers of one hand.

5. The disposable self-contained liquid applicator of claim 1 wherein said member is positioned transversely over an end of said container and forms an underlying supporting surface upon which said membrane is positioned for sealing said container.

6. The disposable self-contained liquid applicator of claim 5 wherein said applicator means is supported by said member underlying said membrane.

7. The disposable self-contained liquid applicator of claim 5 wherein said container and said means for producing a rupturing surface and for penetrating said membrane are formed of a single piece of molded material.

8. The disposable self-contained liquid applicator of claim 7 wherein the cross-section of said container and said means for producing a rupturing surface and for penetrating said membrane is substantially T-shaped.

9. The disposable self-contained liquid applicator of claim 7 wherein the end of said container opposite to said membrane is formed with an opening for filling said container with liquids, said end opposite to said membrane being sealably closed after said container is filled with liquids.

10. A disposable self-contained liquid applicator comprising:
    a container for liquids;
    a rupturable membrane for sealing said container;
    absorbent applicator means overlying said membrane for receiving liquid from said container when said membrane is ruptured; and
    means underlying said membrane for producing a rupturing surface and for penetrating said membrane upon actuation by a force applied to the outside of the applicator, wherein said means for producing a rupturing surface and for penetrating said membrane includes:
    two planar sections inclined from each other and intersecting to define a bending line; and
    at least one serrated slit formed in at least one of said sections along said bending line under said membrane; and wherein said at least one slit has teeth-like edges in the plane of at least one of said sections for forming the rupturing surface and penetrating said membrane when said edges are moved outwardly against said membrane said planar sections have outer flange portions extending away from said container and manually movable downwardly and inwardly toward said container for producing said teeth-like edges from the plane of said sections and for moving said edges outwardly against said membrane, said planar sections are positioned transversely over an end of said container and form an underlying supporting surface upon which said membrane is positioned for sealing said end of said container, and wherein said container and said means for producing a rupturing surface and for penetrating said membrane are formed of a single piece of molded material.

11. The disposable self-contained liquid applicator of claim 10 wherein said flange portions may be manually movable by the thumb and fingers of one hand.

12. The disposable self-contained liquid applicator of claim 10 wherein a groove is formed in the under surface of said planar sections along said bending line for ensuring downward and inward movement of said flange portions and outward movement of said produced teeth-like edges against said membrane.

13. The disposable self-contained liquid applicator of claim 10 wherein said applicator means is supported by said planar sections underlying said membrane.

14. The disposable self-contained liquid applicator of claim 10 wherein the cross-section of said container and said means for producing a rupturing surface and for penetrating said membrane is substantially T-shaped.

15. The disposable self-contained liquid applicator of claim 10 wherein the end of said container opposite to said membrane is formed with an opening for filling said container with liquids, said end opposite to said membrane being sealably closed after said container is filled with liquids.

* * * * *